United States Patent [19]

Sanderson et al.

[11] Patent Number: 5,120,891
[45] Date of Patent: Jun. 9, 1992

[54] PROCESS FOR OLIGOMERIZING OLEFINS USING A SUPER-DEALUMINATED Y-ZEOLITE

[75] Inventors: John R. Sanderson, Leander; Pei S. E. Dai, Port Arthur; John F. Knifton, Austin, all of Tex.

[73] Assignee: Texaco Chemical Company, White Plains, N.Y.

[21] Appl. No.: 588,257

[22] Filed: Sep. 26, 1990

[51] Int. Cl.$^5$ ............................................. C07C 2/02
[52] U.S. Cl. ................................. 585/533; 585/255
[58] Field of Search ............................. 585/255, 533

[56] References Cited

U.S. PATENT DOCUMENTS

| | | |
|---|---|---|
| 4,254,295 | 3/1981 | Tabak . |
| 4,263,465 | 4/1981 | Sheng et al. ........................ 585/18 |
| 4,417,088 | 11/1983 | Miller . |
| 4,430,516 | 2/1984 | LaPierre et al. ..................... 585/533 |
| 4,538,012 | 8/1985 | Miller . |
| 4,628,139 | 12/1986 | Barnett . |
| 4,855,528 | 8/1986 | Young et al. . |
| 4,876,411 | 10/1986 | Bowes et al. . |
| 4,912,280 | 3/1990 | Clerici . |

FOREIGN PATENT DOCUMENTS 0261730 of 0000 European Pat. Off. .

OTHER PUBLICATIONS

D. A. Whan, "Structure and Catalytic Activity of Zeolites", Chemistry in Britain, pp. 532–535.
D. W. Breck and R. A. Sunderson, "Molecular Sieves"-'Encyclopedia of Chemical Technology, Kirk–Othmer, vol. 15 (1981).

*Primary Examiner*—Patrick P. Garvin
*Assistant Examiner*—E. D. Irzinski
*Attorney, Agent, or Firm*—Jack H. Park; Kenneth R. Priem; Russell R. Stolle

[57] ABSTRACT

An improved process is disclosed for preparing synthetic lubricant base stocks. Synthetic lubricant base stocks are prepared in good yield by oligomerizing linear olefins using a catalyst comprising a super-dealuminated Y-zeolite.

17 Claims, No Drawings

PROCESS FOR OLIGOMERIZING OLEFINS USING A SUPER-DEALUMINATED Y-ZEOLITE

BACKGROUND OF THE INVENTION

1. Field of the Invention

The invention relates to the preparation of synthetic lubricant base stocks, and more particularly to synthetic lubricant base stocks made by oligomerizing long-chain linear olefins.

2. Description of Related Methods

Synthetic lubricants are prepared from man-made base stocks having uniform molecular structures and, therefore, well-defined properties that can be tailored to specific applications. Mineral oil base stocks, on the other hand, are prepared from crude oil and consist of complex mixtures of naturally occurring hydrocarbons. The higher degree of uniformity found in synthetic lubricants generally results in superior performance properties. For example, synthetic lubricants are characterized by excellent thermal stability. As automobile engines are reduced in size to save weight and fuel, they run at higher temperatures, therefore requiring a more thermally stable oil. Because lubricants made from synthetic base stocks have such properties as excellent oxidative/thermal stability, very low volatility, and good viscosity indices over a wide range of temperatures, they offer better lubrication and permit longer drain intervals, with less oil vaporization loss between oil changes.

Synthetic base stocks may be prepared by oligomerizing internal and alpha-olefin monomers to form a mixture of dimers, trimers, tetramers, and pentamers, with minimal amounts of higher oligomers. The unsaturated oligomer products are then hydrogenated to improve their oxidative stability. The resulting synthetic base stocks have uniform isoparaffinic hydrocarbon structures similar to high quality paraffinic mineral base stocks, but have the superior properties mentioned due to their higher degree of uniformity.

Synthetic base stocks are produced in a broad range of viscosity grades. It is common practice to classify the base stocks by their viscosities, measured in centistokes (cSt) at 100° C. Those base stocks with viscosities less than or equal to about 4 cSt are commonly referred to as "low viscosity" base stocks, whereas base stocks having a viscosity in the range of around 40 to 100 cSt are commonly referred to as "high viscosity" base stocks. Base stocks having a viscosity of about 4 to about 8 cSt are referred to as "medium viscosity" base stocks. The low viscosity base stocks generally are recommended for low temperature applications. Higher temperature applications, such as motor oils, automatic transmission fluids, turbine lubricants, and other industrial lubricants, generally require higher viscosities, such as those provided by medium viscosity base stocks (i.e. 4 to 8 cSt grades). High viscosity base stocks are used in gear oils and as blending stocks.

The viscosity of the base stocks is determined by the length of the oligomer molecules formed during the oligomerization reaction. The degree of oligomerization is affected by the catalyst and reaction conditions employed during the oligomerization reaction. The length of the carbon chain of the monomer starting material also has a direct influence on the properties of the oligomer products. Fluids prepared from short-chain monomers tend to have low pour points and moderately low viscosity indices, whereas fluids prepared from long-chain monomers tend to have moderately low pour points and higher viscosity indices. Oligomers prepared from long-chain monomers generally are more suitable than those prepared from shorter-chain monomers for use as medium viscosity synthetic lubricant base stocks.

One known approach to oligomerizing long-chain olefins to prepare synthetic lubricant base stocks is to contact the olefin with boron trifluoride together with a promotor at a reaction temperature sufficient to effect oligomerization of the olefin. See, for example, co-assigned U.S. Pat. Nos. 4,400,565; 4,420,646; 4,420,647; and 4,434,308. However, boron trifluoride gas ($BF_3$) is a pulmonary irritant, and breathing the gaseous fumes formed by hydration of the gas with atmospheric moisture poses hazards preferably avoided. Thus, a method for oligomerizing long-chain olefins using a less hazardous catalyst would be an improvement in the art.

Applicants have discovered, surprisingly, that a high conversion of long-chain olefin to oligomer may be obtained by contacting the olefin with a catalyst comprising a Y-zeolite with a high silica/alumina ratio. In addition to being excellent catalysts, these super-dealuminated Y-zeolites are less hazardous and more easily handled than boron triflouride. These catalysts also provide synthetic lubricant base stocks which have a high dimer/trimer ratio, which is a desirable characteristic for some applications. European Patent Application 0 261 730 discloses oligomerizing olefins having between 4 and 24 carbon atoms using X and Y type zeolites. However, the EP patent application requires the zeolites to be in acid form and partially exchanged with salts of metals, and discloses that the zeolites have a silica to alumina ratio of less than 4:1. Applicants have discovered that a higher conversion may be obtained without having to exchange the zeolites with metal salts by using zeolites having a high silica to alumina ratio.

SUMMARY OF THE INVENTION

The invention relates to a process for the preparation of oligomers, comprising contacting a linear olefin containing from 10 to 24 carbon atoms with a Y-zeolite having a silica to alumina ratio greater than about 5:1.

DESCRIPTION OF THE PREFERRED EMBODIMENTS

The olefin monomer feed stocks used in the present invention may be selected from compounds comprising (1) alpha-olefins having the formula $R''CH=CH_2$, where $R''$ is an alkyl radical of 8 to 22 carbon atoms, and (2) internal olefins having the formula $RCH=CHR'$, where R and R' are the same or different alkyl radicals of 1 to 21 carbon atoms, provided that the total number of carbon atoms in any one olefin shall be within the range of 10 to 24, inclusive. A preferred range for the total number of carbon atoms in any one olefin molecule is 12 to 18, inclusive, with an especially preferred range being 14 to 18, inclusive. If a bottoms product synthetic lubricant with a better volatility is desired, the range for the total number of carbon atoms in any one olefin should be 16 to 18, inclusive. Mixtures of internal and alpha-olefins may be used, as well as mixtures of olefins having different numbers of carbon atoms, provided that the total number of carbon atoms in any one olefin shall be within the range of 10 to 24, inclusive. The alpha and internal-olefins to be oligomerized in this invention may be obtained by processes well-known to those skilled in the art and are commercially available.

The oligomerization reaction may be represented by the following general equation:

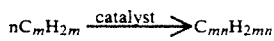

where n represents moles of monomer and m represents the number of carbon atoms in the monomer. Thus, the oligomerization of 1-decene may be represented as follows:

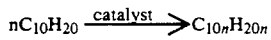

The reaction occurs sequentially. Initially, olefin monomer reacts with olefin monomer to form dimers. The dimers that are formed then react with additional olefin monomer to form trimers, and so on. This results in an oligomer product distribution that varies with reaction time. As the reaction time increases, the olefin monomer conversion increases, and the selectivities for the heavier oligomers increase. Generally, each resulting oligomer contains one double bond.

The catalysts used to effect this reaction are crystalline aluminosilicate zeolites. Zeolites are complex, crystalline inorganic polymers based on an extended framework of $AlO_4$ and $SiO_4$ tetrahedra linked to each other through bridges of oxygen ions. The tetrahedra framework contains interconnected voids that are occupied by the cations—which are mobile and may undergo ion exchange—and water molecules. The water may be removed, generally be heat, which leaves intact a crystalline structure permeated by micropores which may amount to 50% of the crystals by volume.

The structural formula of a zeolite is based on the crystal unit cell, the smallest unit of structure, which may be represented by the following formula:

$$M_{x/n}[(AlO_2)_x(SiO_2)_y] \cdot wH_2O$$

where n is the valence of cation M, w is the number of water molecules per unit cell, and x and y are the total number of tetrahedra per unit cell. The typical cell content of a Y-zeolite in the hydrated form may be represented by the following formula:

$$Na_{56}[(AlO_2)_{56}(SiO_2)_{136}] \cdot 250H_2O$$

Y-zeolites are distinguished from X-zeolites on the basis of the relative concentration of silicon and aluminum atoms and the consequent effects on detailed structure and related chemical and physical properties. Thus, the typical cell content of an X-zeolite may be represented by the following formula:

$$Na_{86}[(AlO_2)_{86}(SiO_2)_{106}] \cdot 264H_2O$$

Catalysts useful in the present invention include Y-zeolites, and in particular those having a high silica to alumina ratio, i.e. a silica to alumina ratio greater than about 5:1. Preferably, the super-dealuminated Y-zeolite has a silica to alumina ratio greater than about 10:1. More preferably, the super-dealuminated Y-zeolite has a silica to alumina ratio of about 40:1 or greater. It is especially preferred that the super-dealuminated Y-zeolite have a silica to alumina ratio of about 60:1 or greater. Such "super-dealuminated" Y-zeolites may be obtained by dealuminating a Y-zeolite by hydrothermal treatment, by mineral acid treatment, or by treatment with ethylenediaminetetraacetic acid (EDTA) or other chelating agents. An example of a suitable, commercially available catalyst is PQ Corporation's CP304-37, having a silica to alumina ratio of about 11:1. An especially preferred catalyst is PQ Corporation's CP301-26, having a silica to alumina ratio of about 60:1.

The catalysts may be in the form of powders, pellets, granules, spheres, shapes or extrudates. The Y-zeolites may be employed alone or, to ensure greater physical strength and stability when in the form of extrudates, pellets, or granules, etc., also may be used in the presence of certain binders. Suitable binders include silica-alumina binders, alumina binders, and carbon binders. Preferably, the catalyst is of high purity; however, it may contain impurities, such as alkali metals (e.g. sodium or potassium), or alkaline earth metals, such as calcium or the like.

The oligomerization reaction may be carried out in either a stirred slurry reactor or in a fixed bed continuous flow reactor. The catalyst concentration should be sufficient to provide the desired catalytic effect. The temperatures at which the oligomerization may be performed are between about 50° and 300° C., with the preferred range being about 120° to 250° C. The reaction may be run at pressures of from 0 to 1000 psig.

Following the oligomerization reaction, the unsaturated oligomers may be hydrogenated to improve their thermal stability and to guard against oxidative degradation during their use as lubricants. The hydrogenation reaction for 1-decene oligomers may be represented as follows:

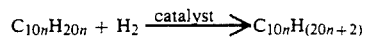

where n represents moles of monomer used to form the oligomer. Hydrogenation processes known to those skilled in the art may be used to hydrogenate the oligomers. A number of metal catalysts are suitable for promoting the hydrogenation reaction, including nickel, platinum, palladium, copper, and Raney nickel. These metals may be supported on a variety of porous materials such as kieselguhr, alumina, or charcoal, or they may be formulated into a bulk metal catalyst. A particularly preferred catalyst for this hydrogenation is a nickel-copper-chromia catalyst described in U.S. Pat. No. 3,152,998, incorporated by reference herein. Other U.S. patents disclosing known hydrogenation procedures include U.S. Pat. Nos. 4,045,508; 4,013,736; 3,997,622; and 3,997,621.

Unreacted monomer may be removed either prior to or after the hydrogenation step. Optionally, unreacted monomer may be stripped from the oligomers prior to hydrogenation and recycled to the catalyst bed for oligomerization. The removal or recycle of unreacted monomer or, if after hydrogenation, the removal of non-oligomerized alkane, should be conducted under mild conditions using vacuum distillation procedures known to those skilled in the art. Distillation at temperatures exceeding 250° C. may cause the oligomers to break down in some fashion and come off as volatiles. Preferably, therefore, the reboiler or pot temperature should be kept at or under about 225° C. when stripping out the monomer. Procedures known by those skilled in the art to be alternatives to vacuum distillation also may be employed to separate unreacted components from the oligomer.

While it is known to include a distillation step after the hydrogenation procedure to obtain products of various 100° C. viscosities, it is preferred in the method of the present invention that no further distillation (beyond monomer flashing) be conducted. In other words, the monomer-stripped, hydrogenated bottoms are the desired synthetic lubricant components. Thus, the method of this invention does not require the costly, customary distillation step, yet, surprisingly, produces a synthetic lubricant component that has excellent properties and that performs in a superior fashion. However, in some contexts, one skilled in the art may find subsequent distillation useful in the practice of this invention.

The invention will be further illustrated by the following examples, which are given by way of illustration and not as limitations on the scope of this invention. The entire text of every patent, patent application or other reference mentioned above is hereby incorporated herein by reference.

EXAMPLES

In the examples detailed below, the following procedure was used:

Oligomerization of Olefins

Reactants and catalyst were charged to a three-necked flask equipped with an overhead stirrer, thermometer, heating mantle, and a water-cooled condenser ($N_2$ purge). The catalysts were a fine powder, or were ground to a fine powder before use. The mixture was vigorously stirred and heated to the desired temperature for the desired time. The mixture was then cooled to ambient temperature and filtered with suction. The liquid was analyzed by liquid chromatography. The results are detailed in the table that follows.

| Oligomerization of Olefins Using Super-dealuminated Y-Zeolites | | | | | | | | |
|---|---|---|---|---|---|---|---|---|
| Ex. No. | Olefin | Catalyst | Wt. % Cat. | Silica/ Alumina Ratio | Time/Temp (Hr/°C.) | Con. (%) | Dimer (%) | Trimer+ (%) | Dimer/ Trimer+ Ratio |
| 1 | C-14A | CP300-56 | 10 | 6.5 | 5.0/160 | 22.4 | 20.3 | 2.13 | 9.53 |
| 2 | C-14A | CP300-56 | 10 | 6.5 | 4.0/180 | 41.9 | 36.0 | 4.90 | 7.35 |
| 3 | C-14A | CP301-26 | 10 | 60 | 5.0/160 | 79.4 | 68.0 | 11.4 | 5.96 |
| 4 | C-14A | CP301-26 | 10 | 60 | 4.0/180 | 79.8 | 67.4 | 12.3 | 5.48 |
| 5 | C-14A | CP301-26 | 10 | 60 | 4.0/200 | 79.3 | 67.7 | 11.6 | 5.83 |
| 6 | C-12A | CP301-26 | 10 | 60 | 5.0/160 | 85.5 | 68.7 | 16.8 | 4.09 |
| 7 | C-12A | CP301-26 | 10 | 60 | 4.0/180 | 87.9 | 69.4 | 18.5 | 3.75 |
| 8 | C-1314 | CP301-26 | 10 | 60 | 4.0/180 | 76.1 | 67.4 | 8.72 | 7.73 |
| 9 | C-14A | CP304-37 | 10 | 11 | 5.0/160 | 42.3 | 40.5 | 1.86 | 21.8 |
| 10 | C-14A | CP304-37 | 10 | 11 | 4.0/180 | 57.5 | 54.2 | 3.40 | 15.9 |
| 11 | C-14A | CP704 | 10 | 40 | 5.0/160 | 76.5 | 68.8 | 7.76 | 8.87 |
| 12 | C-14A | CP704 | 10 | 40 | 4.0/180 | 77.9 | 68.0 | 9.80 | 6.93 |
| 13 | C-14A | Z400H | 10 | 10 | 5.0/160 | 7.93 | 6.54 | 1.39 | 4.70 |
| 14 | C-14A | Z400H | 10 | 10 | 4.0/180 | 18.7 | 15.0 | 3.73 | 4.02 |
| 15 | C-14A | Z700H | 10 | 10 | 5.0/160 | 5.74 | 2.99 | 2.74 | 1.09 |
| 16 | C-14A | Z700H | 10 | 10 | 4.0/180 | 5.96 | 4.04 | 1.92 | 2.10 |

A = alpha; 1314 = tridecene/tetradecene internal olefin mix; CP301-26, CP304-37, and CP704 are sold under Valfor ® label by PQ Corporation; Z400H and Z700H were obtained from Norton Chemical; Con. = conversion; and Trimer+ = trimer + tetramer + pentamer, etc.

We claim:

1. A process for the preparation of oligomers, comprising contacting a linear olefin containing from 12 to 24 carbon atoms with a catalyst comprising a Y-zeolite having a silica to alumina ratio greater than about 5:1.

2. The process of claim 1, wherein the Y-zeolite has a silica to alumina ratio greater than about 10:1.

3. The process of claim 1, wherein the Y-zeolite has a silica to alumina ratio of about 40:1 or greater.

4. The process of claim 1, wherein the Y-zeolite has a silica to alumina ratio of about 60:1 or greater.

5. The process of claim 1, wherein the linear olefin contains from 12 to 18 carbon atoms.

6. The process of claim 1, wherein the linear olefin contains from 14 to 18 carbon atoms.

7. The process of claim 1, wherein the linear olefin contains from 16 to 18 carbon atoms.

8. A process for the preparation of oligomers, comprising contacting a linear olefin containing from 14 to 18 carbon atoms with a catalyst comprising a Y-zeolite having a silica to alumina ratio of about 40:1 or greater.

9. The process of claim 8, wherein the Y-zeolite has silica to alumina ratio of about 60:1 or greater.

10. The process of claim 8, wherein the olefin contains from 16 to 18 carbon atoms.

11. A process for the preparation of a synthetic lubricant base stock, comprising the following steps:
(a) contacting a linear olefin containing from 12 to 24 carbon atoms with a catalyst comprising a Y-zeolite having a silica to alumina ratio greater than about 5:1; (b) separating out any remaining un-oligomerized olefin; and (c) hydrogenating the oligomer fraction resulting from step (b) to produce a synthetic lubricant base stock.

12. The process of claim 11, wherein the olefin contains from 12 to 18 carbon atoms.

13. The process of claim 11, wherein the linear olefin contains from 14 to 18 carbon atoms.

14. The process of claim 11, wherein the linear olefin contains from 16 to 18 carbon atoms.

15. The process of claim 11, wherein the Y-zeolite has a silica to alumina ratio greater than about 10:1.

16. The process of claim 11, wherein the Y-zeolite has a silica to alumina ratio of about 40:1 or greater.

17. The process of claim 11, wherein the Y-zeolite has a silica to alumina ratio of about 60:1 or greater.

* * * * *